US007595176B2

(12) United States Patent
Loeffler et al.

(10) Patent No.: US 7,595,176 B2
(45) Date of Patent: Sep. 29, 2009

(54) **METHODS AND REAGENTS FOR QUANTITATIVE ANALYSIS OF *DEHALOCOCCOIDES* SPECIES**

(75) Inventors: Frank Loeffler, Atlanta, GA (US); Kirsti M. Ritalahti, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 55 days.

(21) Appl. No.: 10/558,965

(22) PCT Filed: May 27, 2004

(86) PCT No.: PCT/US2004/016978

§ 371 (c)(1),
(2), (4) Date: Nov. 30, 2005

(87) PCT Pub. No.: WO2004/108965

PCT Pub. Date: Dec. 16, 2004

(65) Prior Publication Data

US 2007/0105106 A1   May 10, 2007

Related U.S. Application Data

(60) Provisional application No. 60/474,831, filed on May 30, 2003.

(51) Int. Cl.
*C12Q 1/68* (2006.01)
*C12P 19/34* (2006.01)
(52) U.S. Cl. .......................... 435/91.2; 435/6; 435/91.1
(58) Field of Classification Search .................. None
See application file for complete search history.

(56) References Cited

U.S. PATENT DOCUMENTS

| 4,683,195 | A | 7/1987 | Mullis et al. | |
|---|---|---|---|---|
| 4,683,202 | A | 7/1987 | Mullis | |
| 4,800,159 | A | 1/1989 | Mullis et al. | |
| 4,965,188 | A | 10/1990 | Mullis et al. | |
| 6,387,652 | B1 * | 5/2002 | Haugland et al. | 435/34 |
| 6,518,025 | B1 | 2/2003 | Steinborn et al. | |

FOREIGN PATENT DOCUMENTS

| EP | 0 201 184 | | 8/2004 |
|---|---|---|---|
| WO | WO 00/63443 | | 10/2000 |
| WO | WO 00/63443 A2 | * | 10/2000 |

OTHER PUBLICATIONS

Buck et al., "Design Strategies and Performance of Custom DNA Sequencing Primers," BioTechniques, Sep. 1999, vol. 27, pp. 528-536.*
Campbell et al., Environ. Toxicol. Chem., 1977,16 : 625-630.
Allen-King, et al., Environ. Toxicol. Chem., 1997,16 : 424-429.
Abelson, Science, 1990,250 : 733.
DiStefano, et al. , Appl. Environ. Microbiol., 1991,57 : 2287-2292.
Freedman, et al. Appl. Environ. Microbiol., 1989,55 : 2144-2151.
Vogel, et al., Appl. Environ. Microbiol., 1985, 49: 1080-1083.
Maymó-Gatell, et al. , Appl. Environ. Microbiol., 1995,61 : 3928-3933.
Kielhorn, et al., Environ. Health Perspect., 2000,108 : 579-588.
Coulston, et al., Regul. Toxicol. Pharmocol., 1994,19 : 344-348.
Löffler et al., Appl. Environ. Microbiol., 1996,62 : 3809-3813.
Holliger et al., FEMSMicrobiol. Rev. 1999, 22: 383-398.
Löffler et al., Appl. Environ. Microbiol., 2000,66 : 1369-1374.
Flynn et al., Environ. Sci. Technol., 2000,34 : 1056-1061.
Löffler et al., Appl. Environ. Microbiol., 1999 65: 4049-4056.
Rosner et al., Appl. Environ. Microbiol., 1997,63 : 4139-4144.
Hendrickson et al., Appl. Environ. Microbiol., 2002, 68 : 485-495.
Heid et al., Genome Research, 1996,6 : 986-994.
He et al., Environ. Sci. Technol. 2002, 36 : 3945-3952.
Lendvay et al., Environ. Sci. Technol., 2003, 37 : 1422-1431.
Löffler et al., Appl. Environ. Microbiol., 1997,63 : 4982-4985.
Zehnder et al., Science, 1976,194 : 1165-1166.
Gossett, Environ. Sci. Technol., 1987,21 : 202-208.
Magnuson et al. , Appl. Environ. Microbiol., 2000,66 : 5141-5147.
Altschul et al., J. Mol. Biol., 1990,215 : 403-410.
Adrian et al., Nature, 2000, 408: 580-583.
Maymo-Gatell et al., Science, 1997,276 : 1568-1571.
Maymó-Gatell et al., Appl. Environ. Microbiol., 1999,65 : 3108-3113.
Maymo-Gatell et al., Environ. Sci., Technol., 2001,35 : 516-521.
Duhamel et al., Water Res., 2002,36 : 4193-4202.
Sanford et al., Appl. Environ. Microbiol, 2002,68 : 893-900.
EPA, Agency for Toxic Substances and Disease Registry, ToxFAQs for chlorinated ethenes. 1996; www.atsdr.cdc.gov/tfacts70.html.
Maidak et al., Nucleic Acid Res., 2001, 29:173-174.
Wilson, J.T. et al.; "A Review of Intrinsic Bioremediation of Trichloroethylene in Ground Water at Picatinny Arsenal, New Jersey, and St. Joseph, Michigan"; U.S. EPA, Symposium on Bioremediation of Hazardous Wastes: Research, Development, and Field Evaluations; Aug. 8-10, 1995; pp. 11-14; Rye Brook, NY; EPA/600/R-95/076.
He, Jianzhong et al., "Complete Detoxification of Vinyl Chloride by an Anaerobic Enrichment Culture and Identification of the Reductively Dechlorinating Population as a Dehalococcoides Species", Applied and Environmental Microbiology, vol. 69, No. 2, (Feb. 2003), pp. 996- 1003.

* cited by examiner

*Primary Examiner*—Young J Kim
(74) *Attorney, Agent, or Firm*—Darby & Darby P.C.

(57) ABSTRACT

The invention sets forth specific probes and primer pairs for such quantitative analysis and methods of obtaining template DNA from the *Dehalococcoides* species of interest. These techniques are useful in a bioremediation process to monitor and control the dechlorination of chlorinated hydrocarbons.

20 Claims, No Drawings

SEQUENCE LISTING

```
<160> NUMBER OF SEQ ID NOS: 5

<210> SEQ ID NO 1
<211> LENGTH: 25
<212> TYPE: DNA
<213> ORGANISM: artificial
<220> FEATURE:
<223> OTHER INFORMATION: probe

<400> SEQUENCE: 1
tcctcagttc ggattgcagg ctgaa                                          25

<210> SEQ ID NO 2
<211> LENGTH: 21
<212> TYPE: DNA
<213> ORGANISM: artificial
<220> FEATURE:
<223> OTHER INFORMATION: primer

<400> SEQUENCE: 2
ctggagctaa tccccaaagc t                                              21
```

-continued

```
<210> SEQ ID NO 3
<211> LENGTH: 18
<212> TYPE: DNA
<213> ORGANISM: artificial
<220> FEATURE:
<223> OTHER INFORMATION: primer

<400> SEQUENCE: 3
caacttcatg caggcggg                                                 18

<210> SEQ ID NO 4
<211> LENGTH: 18
<212> TYPE: DNA
<213> ORGANISM: artificial
<220> FEATURE:
<223> OTHER INFORMATION: primer

<400> SEQUENCE: 4
gcggttttct aggttgtc                                                 18

<210> SEQ ID NO 5
<211> LENGTH: 18
<212> TYPE: DNA
<213> ORGANISM: artificial
<220> FEATURE:
<223> OTHER INFORMATION: primer

<400> SEQUENCE: 5
caccttgctg atatgcgg                                                 18
```

METHODS AND REAGENTS FOR QUANTITATIVE ANALYSIS OF *DEHALOCOCCOIDES* SPECIES

This is a U.S. National Phase application under 35 U.S.C. §371 of International Patent Application No. PCT/US04/16978, filed May 27, 2004, which claims the benefit of U.S. Provisional Application No. 60/474,831 filed May 30, 2003, all of which are incorporated by reference herein.

STATEMENT REGARDING FEDERALLY SPONSORED RESEARCH OR DEVELOPMENT

Research and development leading to certain aspects of the present invention were supported, in part, by research grants from the United States Army (DACA72-00-C-0023) and the National Science Foundation (IBN-0090496). The U.S. government may have certain rights in this invention.

FIELD OF THE INVENTION

This invention relates to techniques to measure the level of *Dehalococcoides* species in a sample. More particularly, the invention sets forth techniques for quantifying populations of *Dehalococcoides* using real time polymerase chain reaction ("RTm-PCR") technology.

BACKGROUND OF THE INVENTION

Chlorinated hydrocarbons represent a class of toxic chemicals frequently found at contaminated sites. Perchloroethene (e.g., tetrachloroethylene "PCE") and trichloroethene ("TCE") are choice solvents for numerous applications, but their widespread use has resulted in extensive groundwater contamination. Partial reductive dechlorination of PCE and TCE mediated through abiotic and biotic processes lead to the accumulation of toxic (e.g., dichloroethenes, "DCEs") and carcinogenic (e.g., vinyl chloride, "VC") intermediates. See, e.g., Campbell et al., *Environ. Toxicol. Chem.*, 1977, 16:625-630; Allen-King, et al., *Environ. Toxicol. Chem.*, 1997, 16:424-429; Abelson, *Science*, 1990, 250:733; DiStefano, et al., *Appl. Environ. Microbiol.*, 1991, 57:2287-2292; Freedman, et al. *Appl. Environ. Microbiol.*, 1989, 55:2144-2151; Vogel, et al., *Appl. Environ. Microbiol.*, 1985, 49:1080-1083; Maymó-Gatell, et al., *Appl. Environ. Microbiol.*, 1995, 61:3928-3933. VC has been found in at least 496 of the 1,430 National Priorities List (NPL) sites identified by the U.S. Environmental Protection Agency (EPA). PCE and TCE are present in at least 771 and 852 NPL sites, respectively. See, e.g., EPA, Agency for Toxic Substances and Disease Registry, ToxFAQs for chlorinated ethenes. 1996; on the Worldwide Web at www.atsdr.cdc.gov/tfacts70.html.

Although the main contributions of VC contamination in subsurface environments is through the incomplete reductive dechlorination of PCE and TCE, other contamination sources exist. For example, past incidental releases of VC may have led to local groundwater and soil contamination. For instance, VC is a precursor in the manufacturing of PVC, and in excess of 7 million tons of VC was produced in the United States in 1996. In recent years, the estimated annual VC production in the world was 27 million tons. See, Kielhorn, et al., *Environ. Health Perspect.*, 2000, 108:579-588. PVC is also a suspected source of VC in landfills, where VC is frequently detected in drainage water. See, Coulston, et al., *Regul. Toxicol. Pharmocol.*, 1994, 19:344-348.

The remediation of groundwater contaminated with chlorinated ethenes is challenging. Traditional "pump-and-treat" treatment systems have proven to be ineffective, time-consuming and costly, especially at contaminated sites with complex hydrogeology and large plumes. The discovery that bacterial populations use chlorinated ethenes as electron acceptors, thus efficiently reducing and detoxifying these compounds, has made bioremediation an attractive technique for ground water pollution control. This process, in which bacteria couple the reductive dechlorination process to growth, is known as (de)chlororespiration or chloridogenesis. See e.g., Löffler et al., *Appl. Environ. Microbiol.*, 1996, 62:3809-3813. The physiology and phylogeny of several PCE-to-cis-DCE-dechlorinating bacteria are fairly well understood and have received ample review. See e.g., Holliger et al., *FEMS Microbiol. Rev.* 1999, 22:383-398.

Although the complete microbial reductive dechlorination of chloroethenes to ethene is well documented in microcosms, laboratory cultures, and bioreactors, the nature of the organisms responsible for the final dechlorination step remains elusive. Both *Dehalococcoides ethenogenes* strain 195 and *Dehalococcoides* sp. strain FL2 were shown to reduce VC to ethene, however, the reaction was cometabolic, only occurring when the cultures were grown with a higher chlorinated ethene. Neither population grew with VC alone. See, e.g., Löffler et al., *Appl. Environ. Microbiol.*, 2000, 66:1369-1374. Flynn et al. demonstrated a community shift in response to enrichment with PCE versus cis-DCE or VC. Flynn et al., *Environ. Sci. Technol.*, 2000, 34:1056-1061. Circumstantial evidence strongly suggested that populations that use VC as a metabolic electron acceptor exist. Löffler et al., *Appl. Environ. Microbiol.*, 1999 65:4049-4056; Rosner et al., *Appl. Environ. Microbiol.*, 1997, 63:4139-4144.

Hendrickson et al. detected *Dehalococcoides* 16S rRNA sequences at 21 chloroethene-contaminated sites that produced ethene. Hendrickson et al., *Appl. Environ. Microbiol.*, 2002, 68:485-495. Another study demonstrated that five enrichment cultures that were maintained with VC as electron acceptor, dechlorinated VC to ethene in the absence of polychlorinated ethenes. All five cultures contained at least one *Dehalococcoides* population, as demonstrated with 16S rRNA gene-based approaches. K. M. Ritalahti et al., Abstr. 6th Int. Symp. In situ On-Site Bioremediation, 2001. These findings imply that members of the *Dehalococcoides* cluster with different properties than the PCE/TCE-dechlorinating isolates *Dehalococcoides ethenogenes* strain 195 and *Dehalococcoides* sp. strain FL2 are involved in metabolic VC reductive dechlorination.

It is desired to characterize a VC-to-ethene-dechlorinating enrichment culture obtained from an impacted aquifer or other contamination site, to identify the population(s) catalyzing the dechlorination step, and to demonstrate that VC serves as a growth-supporting electron accepter for the dechlorinating population(s).

This goal, as well as optimal functioning of this bioremediation technique in general, depends on precise quantification of *Dehalococcoides* species, like those discussed above. Thus to there is a need for accurate quantitative analysis of *Dehalococcoides* populations. Such measurements are preferably precise and obtained quickly, thus producing an accurate assessment of *Dehalococcoides* species while reducing lag time.

Previously, PCR-based efforts to quantify *Dehalococcoides* species have employed 5'AAGGCGGTTTTCTAGGTTGTCAC3' (SEQ ID NO: 6) as the forward primer, and 5'CGTTTCGCGGGGCAGTCT3' (SEQ ID NO: 7) as the reverse primer. Löffler, *Appl. Environ. Microbiol.*, 2000, 66:1369-1374. International Publication Number WO 00/63443 sets forth various sequences that can be used as primers and probes said to be useful in the identification of dechlorinating bacteria. These primers were derived from specific segments of the 16S rRNA gene of *Dehalococcoides ethenogenes* (DHE).

Notwithstanding the publication of certain primer sets for PCR amplification of *Dehalococcoides* 16S RNA genes, there remains a need in the art for an efficient real time detection system, particularly one that works in the field. There also is a need for obtaining template DNA for the *Dehalococcoides* species of interest that is suitable for PCR amplification.

In the present application, the inventors describe primers and probes adapted for Real Time PCR, and provide enhanced specificity for *Dehalococcoides,* and are different from the primer pairs and probes known in the art, and methods for preparing samples for RTm-PCR detection of *Dehalococcoides.*

SUMMARY OF THE INVENTION

The present invention provides certain gene primer pairs and probes for *Dehalococcoides* quantification using Real Time PCR technology. The invention further provides for the isolation of target DNA from *Dehalococcoid* species of interest. The components provided and the methods in which they are employed are useful in *Dehalococcoid* bioremediation processes.

Accordingly, provided is a method of quantifying the amount of *Dehalococcoides* species present in a sample comprising, contacting said sample with a probe consisting essentially of the sequence 5'TCCTCAGTTCGGATTGCAGGCTGAA3' (SEQ ID NO: 1); a first primer consisting essentially of 5'CTGGAGCTAATCCCCAAAGCT3' (SEQ ID NO: 2); and a second primer consisting essentially of the sequence 5'CAACTTCATGCAGGCGGG3' (SEQ ID NO: 3); and performing real time PCR on said sample to quantify the amount of said *Dehalococcoides* species.

The present invention further provides a method for preparing DNA from a *Dehalococcoides* for analysis, e.g., for the RTm-PCR analysis described in this application. The method improves the yield and quality of the DNA compared to prior art methods, e.g., manufacturers instructions. The method comprises extracting DNA from a *Dehalococcoides* pellet by cell lysis under extended incubation conditions in the presence of a bacteriolytic enzyme, a protease, and a peptidase so as to increase the yield of DNA from the pellet. In a specific embodiment, the method comprises extracting DNA from a *Dehalococcoides* pellet by cell lysis under incubation conditions for greater than 3 hours, at least 55° C. in the presence of lysozyme, Proteinase K, and a achromopeptidase so as to increase the yield of DNA from the pellet.

A further advantage of the preparation method of the invention comes from repeated rounds of centrifugation to form the *Dehalococcoides* pellet. In one aspect, this further involves adding additional culture fluid prior to each round of centrifugation.

An advantage of this invention is that it provides for lysis of substantially all of the *Dehalococcoides* cells. In contrast, prior art methods did not lyse all *Dehalococcoides* cells, resulting in decreased reproducibility of data. As used herein, the term "substantially all of the *Dehalococcoides* cells" can mean that there are no detectable cells remaining, e.g., by centrifugation. Alternatively, it can mean that greater than 95% of the cells, preferably greater than 99% of the cells, and more preferably greater than 99.9% of the cells are lysed.

These advantages can be employed for other methods of detecting *Dehalococcoides* as well, such as, but not limited to, standard PCR, reverse transcription-PCR, and genomic DNA detection with a probe, e.g., Southern analysis.

DETAILED DESCRIPTION

In the bioremediation techniques disclosed herein, particular emphasis is placed on the *Dehalococcoides* quantification efforts, particularly employing novel primers and probes and improved techniques of obtaining *Dehalococcoides* template DNA, for use in Real Time PCR technology.

RTm-PCR is a further enhancement to the standard PCR that allows contemporaneously outputted quantification of, for example, bacteria populations. PCR involves annealing target DNA into single strands and amplifying the target sequence using the forward and reverse gene primers. See, e.g., U.S. Pat. Nos. 4,683,195; 4,683,2020; 4,965,188; and 4,800,159.

A primer refers to an oligonucleotide that can be extended with a DNA polymerase using monodeoxyribonucleoside triphosphates and a nucleic acid that is used as a template. This primer preferably has a 3' hydroxyl group on an end that is facing the 5' end of the template nucleic acid when it is hybridized with the template.

A set of primers refers to a combination or mixture of at least a first and a second primer. The first primer can be extended using the template nucleic acid while forming an extension product in such a way that the second primer can hybridize with this extension product in a region of the extension product that lies in the 3' direction of the extendable end of the first primer. The extendable end of the second primer points in the 5' direction of the extension product of the first primer. Examples of primers that are suitable for performing the polymerase chain reaction (PCR) and that meet this definition are described in European Patent No. 0201184. Typical amplicons range in size from 25 bp to 2000 bp. See U.S. Pat. No. 6,518,025. Larger sized amplicons can be obtained, typically using specialized conditions or modified polymerases.

In real time PCR, a fluorogenically labeled oligonucleotide probe is also used along with primer sets specific for the target DNA and probe. An oligonucleotide is understood to be a molecule that has a sequence of bases on a backbone comprised mainly of identical monomer units at defined intervals. The bases are arranged on the backbone in such a way that they can enter into a hybridization bond with a nucleic acid having a sequence of bases that are complementary to the bases of the oligonucleotide.

In RTm-PCR, the probe anneals to a sequence on the target DNA found between the forward (5') and reverse (3') PCR primer binding sites and consists of an oligonucleotide with a 5'-reporter dye (e.g., FAM, 6-carboxyfluorescein) and a quencher dye (e.g., TAMRA, 6-carboxytetramethylrhodamine) which quenches the emission spectra of the reporter dye as long as both dyes are attached to the probe. The probe signals the formation of PCR amplicons by a process involving the polymerase-induced nucleolytic degradation of the double-labeled fluorogenic probe that anneals to the target template at a site between the two primer recognition sequences. See, U.S. Pat. No. 6,387,652.

The measurement of the released fluorescent emission continuously during the PCR amplification (Heid et al., *Genome Research,* 1996, 6:986-994) thus forms the basis for quantifying the amount of target nucleic acid present in a sample at the initiation of the PCR reaction. Since the exponential accumulation of the fluorescent signal directly reflects the exponential accumulation of the PCR amplification product, this reaction is monitored in real time. Hardware, such as the model 7700 and model 7900HT Sequence Detection Systems, available from Applied Biosystems, automates the detection and quantitative measurement of these signals, which are stoichiometrically related to the quantities of amplicons produced. From the output data of a so-called Real Time PCR, quantification from a reliable back calculation to the input target DNA sequence is possible using standard curves generated with known amounts of template DNA.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

In accordance with the present invention there may be employed conventional molecular biology, microbiology, and recombinant DNA techniques within the skill of the art. The general genetic engineering tools and techniques discussed herein, including transformation and expression, the use of host cells, vectors, expression systems, etc., are well known in the art. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al. 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

EXAMPLES

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Example 1

Quantification of a Dechlorinating Bacterium

Materials and Methods

Chlorinated ethenes and other chemicals were purchased from Aldrich (Milwaukee, Wis.) and Sigma Chemical Co. (St. Louis, Mo.). $H_2$ was obtained from Air Products (Atlanta, Ga.). Vinyl chloride (VC) was obtained from Fluka Chemical Corp. (Ronkonkoma, N.Y.), and ethene was purchased from Scott Specialty Gases (Durham, N.C.).

Source of Dechlorinating Culture

A sediment-free culture (referred to as the Bachman culture) was derived from PCE-to-ethene-dechlorinating microcosms established with aquifer material from the chloroethene-contaminated Bachman Road site in Oscoda, Mich. He et al., *Environ. Sci. Technol.* 2002, 36: 3945-3952; Lendvay et al., *Environ. Sci. Technol.*, 2003, 37:1422-1431.

Growth Medium and Culture Conditions

All experiments were carried out in serum bottles (160 ml nominal volume) containing 100 ml (final volume) of growth medium, which were sealed with black butyl rubber septa (Wheaton, Ochelata, Okla.). Anoxic, bicarbonate-buffered mineral salts medium was prepared, and was amended with pyruvate (10 mM), lactate (5 mM or 10 mM), acetate plus formate (5 mM each), or acetate (5 mM) as substrates. Löffler et al., *Appl. Environ. Microbiol.*, 1997, 63:4982-4985. Unless indicated otherwise, $H_2$ was only added to acetate-fed cultures at a partial pressure of 9 kPa. Routinely, L-cysteine and $Na_2S \times 9\ H_2O$ (0.2 mM each) were used to chemically reduce the medium. DL-dithiothreitol (DTT) was tested at 0.5 mM concentration. Titanium(III) (0.5 mM) was added from a filter-sterilized citrate solution after the medium had been autoclaved. Löffler et al., *Appl. Environ. Microbial.*, 1996, 62:3809-3813; Zehnder et al., *Science*, 1976, 194:1165-1166. Gaseous VC was added as a single dose of 1 to 6 ml per serum bottle resulting in initial aqueous concentrations ranging from 0.27 to 1.6 mM. Other chloroethenes were added using Hamilton glass syringes (Hamilton, Reno, Nev.) to initial aqueous concentrations ranging from 0.2 to 0.5 mM. Biogenic cis-DCE was produced from PCE (0.5 mM) using a culture of '*Desulfuromonas michiganensis*'.

After complete dechlorination to cis-DCE (0.5 mM), the cultures were amended with pyruvate and inoculated with the VC-dechlorinating culture. New cultures were routinely seeded with a 2% (vol/vol) inoculum using plastic syringes. To minimize the contact of the inoculum with air present in the plastic of the syringes during transfers, the syringes were reduced with a sterile 0.5 mM aqueous sulfide solution for 5-10 min prior to transfers. Gaseous substrates were added with plastic syringes that had been previously flushed with $H_2$- and $O_2$-free $N_2$.

All experiments were set up in triplicates, and all results were verified by at least one additional independent experiment. Culture bottles were incubated upside down at room temperature (22-25° C.) without agitation in the dark, unless indicated otherwise. Duplicate controls (no inoculum or autoclaved inoculum) accompanied each experiment. Ethene formation strictly depended on a viable inoculum, and loss of VC through the septum was negligible.

Analytical Methods and Data Analysis

Chloroethenes were measured with a Hewlett Packard model 6890 gas chromatograph equipped with a HP-624 column (60 m length, 0.32 mm diameter, 1.8 µm film thickness) and a flame ionization detector (FID). Headspace samples of 100 µl were withdrawn with gas-tight 250 µl Hamilton glass syringes with Teflon-lined valves (model # 1725), and manually injected into a split injector operated at a split ratio of 2:1. All syringes were flushed with $H_2$- and $O_2$-free $N_2$ gas to prevent contamination of the cultures with these gases. A temperature program that allowed the simultaneous analysis of all chloroethenes and ethene was described previously. He et al., *Environ. Sci. Technol.*, 2002, 36: 3945-3952. Standards were prepared as described and 7-point calibration curves were established for all chloroethenes and ethene at room temperature. Gossett, *Environ. Sci. Technol.*, 1987, 21: 202-208. The instrument detection limits for VC and ethene were 7.3 and 8.6 µM, respectively. For quantification of VC and ethene at different temperatures, concentrations of each compound were determined from 3-point calibration curves.

Organic acids were monitored by HPLC using a Waters Breeze system (Waters, Milford, Mass.) equipped with a Waters 2487 dual wavelength absorbance detector (set to 210 nm), and a Waters 717 plus autosampler (50 µl injection volume). The eluent was 5 mM aqueous $H_2SO_4$, which was pumped at a flow rate of 0.5 ml min$^{-1}$ through a heated (60° C.) Aminex HPX-87H Ion Exclusion organic acid analysis column (300 mm×7.8 mm) (Bio-Rad, Hercules, Calif.). Aqueous samples (1 ml) were periodically withdrawn from the cultures by syringe and frozen immediately at −20° C. Before analysis, solids were removed from the samples by centrifugation in a microcentrifuge (14,000 rpm, 10 minutes). Samples of the supernatant (475 µl) were transferred to autosampler vials, acidified with 25 µl of 1 M $H_2SO_4$, and mixed before analysis.

Five-point calibration curves were established for each analyte. $H_2$ was quantified with a RGA3 reduction gas analyzer (Trace Analytical, Menlo Park, Calif.) as described Löffler et al., *Appl. Environ. Microbiol.*, 1999, 65: 4049-4056. The standard errors for all analytical measurements were below 15% of the averaged values.

The Monod equation:

$$-\frac{dS}{dt} = \frac{kXS}{S + K_S}$$

was used to describe the substrate reaction kinetics, where S is the chloroethene concentration, $K_S$ is the half-saturation coefficient, k is the maximum chloroethene dechlorination rate per unit of biomass, and X is the dechlorinating biomass concentration. It was assumed that $X_{lag}$ was zero during the lag period due to the small inoculum transferred, and X remained constant during the phase of active dechlorination due to slow growth of the dechlorinating population(s).

Electron donors were added in excess and never became limiting during the period of kinetic data collection. Exploratory experiments demonstrated that chloroethenes were added in concentration ranges not causing inhibitory effects (e.g., prolonged lag time or decreased dechlorination rates). The reduced product ethene had no apparent inhibitory effects on VC dechlorination at the concentrations observed in the cultures. After integration of the Monod equation, nonlinear regression analysis was performed to determine the upper limits for kinetic parameters (i.e. KS and kX).

The distributions of chloroethenes in the gas and liquid phases were calculated according to M=CwVw+CgVg=Cw (Vw+HcVg), where M is the total chloroethene mass (µmol), Cw is the concentration of chloroethene in the liquid phase (µmol/L), Cg is the concentration of chloroethene in the gas phase (µmol/L), Vw is the volume of liquid in the system (L), Vg is the headspace volume of the system (L), and Hc is the dimensionless Henry's constant. Dimensionless Henry coefficients for cis-DCE, trans-DCE, 1,1-DCE, and VC at 25° C. are 0.167, 0.384, 1.069, and 1.137, respectively. Gossett, *Environ. Sci. Technol.*, 1987, 21:202-208.

Extracting the Template DNA

Culture fluid (20 ml) from *Dehalococcoides* species was filtered through 0.2-µm (pore size) polycarbonate membranes, and after suspension of the biomass in TE buffer (10 mM Tris, 1 mM EDTA, pH 8.0) genomic DNA was extracted by using the Qiagen Mini Kit (Qiagen, Valencia, Calif.). The purification procedure was performed according to the manufacturer's recommendations, except that 45 µl of proteinase K (25 mg/ml), 20 µl of lysozyme (100 mg/ml), and 10 µl of a chromopeptidase (25 mg/ml) were used to improve cell lysis.

The quality of the extracted genomic community DNA was verified on 1% agarose gels, and DNA was quantified spectrophotometrically. *Dehalococcoides* 16S rRNA genes were detected in direct PCR by using the *Dehalococcoides*-targeted primer pair 5'-GCG GTT TTC TAG GTT GTC-3' (Dhc 730F; SEQ ID NO: 4) and 5'-CAC CTT GCT GAT ATG CGG-3' (Dhc 1350R; SEQ ID NO: 5), yielding a 620-bp amplicon as described previously. Löffler et al., *Appl. Environ. Microbiol.*, 2000, 66:1367-1374, M. Bunge, et al., *Abstr. Annu Meet. German Soc. Gen. Appl. Microbiol.* 2001, abstr. PSA17, p. 64, 2001.

Clone libraries of 16S rRNA genes were established by using genomic DNA from VC-dechlorinating cultures and the TOPO TA cloning kit (Invitrogen, Carlsbad, Calif.) as described previously. Löffler et al., *Appl. Environ. Microbiol.*, 2000, 66:1367-1374. *E. coli* clones with a 16S rRNA gene insert were screened with the *Dehalococcoides*-targeted primer pair, and plasmid DNA was extracted from positive *E. coli* clones by using the QIAprep Spin Miniprep kit (Qiagen) according to the manufacturer's recommendations. Negative controls consisted of PCRs with no added template DNA, genomic DNA, or plasmid DNA with a 16S rRNA gene insert from "*Desulfuromonas michiganensis*" strain BB1 or an *Acetobacterium* species. Positive control PCRs had genomic or plasmid DNA containing a 16S rRNA gene insert from *Dehalococcoides* sp. Strain FL2 as a template. Double-stranded sequence analysis of nearly complete 16S rRNA genes was performed by using previously published sequencing primers with an ABI 3100 genetic analyzer (Applied Biosystems, Foster City, Calif.). Löffler et al., *Appl. Environ. Microbiol.*, 2000, 66:1367-1374. Sequences were assembled and aligned, and base substitutions and percent similarity values were determined by using the Megalign software of the Laser-gene package (DNASTAR, Inc. Madison, Wis.).

The presence of the structural gene (tceA) encoding the TCE reductive dehalogenase was tested by using the primer pair 797F and 2490R designed to target the tceA gene of *D. ethenogenes*. Magnuson et al., *Appl. Environ. Microbiol.*, 2000, 66:5141-5147. Genomic DNA from *D. ethenogenes* strain 195 (kindly supplied by S. Zinder, Cornell University, via F. von Wintzingerode, Humboldt-Universität zu Berlin), and a *Dehalococcoides* sp.-containing, TCE-dechlorinating enrichment culture derived from river sediment that produced VC as dechlorination end product (supplied by B. Griffin, Michigan State University) were used as positive controls. For 16S rRNA gene analyses, the 50- to 2,000-bp ladder from Bio-Rad was used for size estimation of amplicons, and the Marker 3 from MBI Fermentas GmbH (St. Leon-Rot, Germany) was used for the analysis of tceA.

High quality DNA was also obtained using a slightly different procedure. Genomic DNA was obtained from 200 ml of pure and enrichment cultures by repeated rounds of pelleting cells by centrifugation (4,000 rpm, 30 min) in four, 15 ml conical vials. Following centrifugation, the supernatant is removed with a sterile pipette, leaving approximately 0.5 ml of liquid above "the pellet". Additional culture fluid is added and repeated rounds of centrifugation lead to a larger cell pellet. The resulting pellets are suspended in the remaining 0.5 ml of supernatant and combined into 1.5 ml eppendorf tubes for a final round of centrifugation (13,000 rpm for 15 minutes), which will yield one or tow visible cell pellets.

The DNA was extracted from the pellet using the QIAGEN tissue kit according to the manufacturer's recommendations, with the following modifications. Cell lysis was achieved by adding 20 µl lysozyme (100 mg/ml), 45 µl Proteinase K (25 mg/ml), and 10 µl achromopeptidase (7,500 U/ml). The mixture was incubated at 55° C. for 3.5 hours, with an inversion performed at 30 minute intervals. Complete lysis was verified by microscopic examination. The remaining procedures were as described by the manufacturer. DNA was eluted in 200 µl of 10 mM Tris buffer, pH 8.5, and the concentration of isolated DNA was determined spectrophotometrically (see e.g., Sambrook et al.). Isolated DNA was stored at −20° C. The extended incubation time in the presence of lysozyme, Proteinase K and achromopeptidase increased the total yield in obtaining high quality DNA from the cells.

Dehalococcoides Quantification via Real Time PCR

Amplification, and hence precision of RTm-PCR technology, depends on primers and probes specifically chosen to quantify target sequences, here Dehalococcoides species having dechlorination properties.

In general, the genus Dehalococcoides forms a separate phylogenetic lineage, and two of its known members (D. ethenogenes and strain FL2) are not closely affiliated with other known bacteria. These and other Dehalococcoide populations were targeted. The primer pair was designed to detect these strains and therefore be more comprehensive, yet remain specific for the group. Purified DNA from several other chlororespiring bacteria was used as template for the Dehalococcoides-targeted primers. As expected, amplification occurred only when DNA (or cell lysates) of the defined PCE-dechlorinating mixed culture or an E. coli clone containing the 16S rRNA gene of Dehalococcoides sp. strain FL2 was used as a template.

Oligonucleotides targeting 16S rRNA gene sequences of Dehalococcoides ethenogenes, Dehalococcoides sp. strain FL2, and the VC-dechlorinating Dehalococcoides population identified in the Bachman culture (GenBank accession no. AF357918, AF004928, and AY165308, respectively) were designed. The following oligonucleotides were selected, and through research, found to yield surprising and unexpected improvements in quantification of Dehaloccocoides species, including Dehalococcoides sp. strain FL2:

```
SEQ ID NO: 2  5'CTGGAGCTAATCCCCAAAGCT3'
              (forward primer)

SEQ ID NO: 3  5'CAACTTCATGCAGGCGGG3'
              (reverse primer);
and

SEQ ID NO: 1  5'TCCTCAGTTCGGATTGCAGGCTGAA3' (probe)
```

Probe/primer specificity was verified using the Probe Match program of the RDP-II (Ribosomal Database Project) and BLAST analysis. Altschul et al., *J. Mol. Biol.*, 1990, 215: 403-410; Maidak et al., *Nucleic Acid Res.*, 2001, 29:173-174.

The probe contained 6-carboxy-fluorescein (FAM) as a reporter fluorochrome on the 5'end, and N,N,N',N'-tetramethyl-6-carboxy-rhodamine (TAMRA) as quencher on the 3' end. Each MicroAmp optical tube had 30-µl reaction volume containing 1×TaqMan Universal PCR Master Mix (including DNA polymerase, deoxynucleoside triphosphates, and $MgCl_2$) (Applied Biosystems), forward primer, reverse primer, and TaqMan probe (300 nM each), and DNA template from each 10-fold diluted sample. The PCR conditions were as follows: 2 min at 50° C., 10 min at 95° C. followed by 40 cycles of 15 s at 95° C. and 1 min at 60° C. PCR was carried out in a spectrofluorimetric thermal cycler (ABI Prism 7700 Sequence Detection System, Applied Biosystems).

A calibration curve (log DNA concentration versus arbitrarily set cycle threshold value, $C_T$) was obtained using serial dilutions of DNA of known concentration. The $C_T$ values obtained for each sample were compared with the standard curve to determine the DNA concentration of Dehalococcoides. Using an average molecular weight of 660 for a base pair in dsDNA, one 16S rRNA gene operon per Dehalococcoides genome, and a genome size of 1.5 Mbp (www.tigr.org), the following equation was used to ascertain the number of Dehalococcoides-derived 16S rRNA gene copies that were present in the DNA obtained from 1 ml of the dechlorinating enrichment culture:

$$16S\ rRNA\ \text{gene copies/ml} = \frac{DNA\ (\mu g/ml) \times 6.023 \times 10^{23}}{(1.5 \times 10^6 \times 660) \times 10^6}$$

Using these reagents provides precise and accurate quantitation of microbial populations and genes in soils and sediments. The present inventors have found their primer sets to be specific for Dehalococcoides species. None of the other bacterial strains tested resulted in amplification regardless of the template used (cell lysates or isolated genomic DNA). The $r^2$ values for the standard curves were >99 in both pure cultures and in sediment samples. Detection limits of $10^2$ rRNA gene copies per g of aquifer materials were determined for Dehalococcoides spp.

Dechlorination Results.

Sequential transfers from PCE-to-ethene-dechlorinating microcosms to reduced mineral salts medium amended with lactate and VC yielded a sediment-free, ethene-producing enrichment culture. Ethene accumulated as the end product and no further transformation occurred. Methane formation only occurred at initial VC concentrations below 0.3 mM. After three sequential transfers to medium with aqueous VC concentrations above 0.3 mM, no methane formation from methanogenic substrates occurred indicating that methanogenic archaea had been diluted out. During the enrichment process, the lag times before dechlorination started became increasingly variable between replicates, ranging from 10 days to several weeks. Transfers were made with plastic syringes, and we occasionally noticed that the inoculum withdrawn from more enriched cultures turned pink (oxidation of the redox indicator resazurin) inside the syringe during the transfer process. Following this observation, all plastic syringes were reduced with a sulfide solution before cell suspensions were transferred. This procedure did not decrease the lag time but significantly reduced the variability between replicate cultures indicating that the dechlorinating population(s) was very sensitive to $O_2$.

The sediment-free, nonmethanogenic culture was transferred more than 40 times in defined bicarbonate-buffered mineral salts medium with lactate and VC, which was consistently reduced to stoichiometric amounts of ethene within 4 to 8 weeks. Pyruvate and $H_2$ also supported visible growth and dechlorination to ethene. The dechlorination of VC to ethene occurred in a culture with pyruvate as the electron donor. Pyruvate was completely consumed before VC reductive dechlorination started, indicating that pyruvate was not the direct electron donor for VC dechlorination. Substantial amounts of $H_2$ (>1 kPa) were formed during the fermentation of pyruvate and the oxidation of formate, which accumulated transiently. After 50 days, the initial amount of 275 µmol VC was completely reduced to ethene, and the headspaces of triplicate cultures were exchanged with $H_2$-free $N_2/CO_2$ (80/20 [vol/vol]). Another 275 µmol VC, along with 223 µmol $H_2$, were added, and dechlorination started without an apparent lag time, however, ethene formation slowed down after approximately 20 days. At this time, the $H_2$ concentrations in the cultures had dropped below 0.5 ppmv indicating that H$_2$ became limiting. When H$_2$ was added to these cultures, high rate dechlorination continued without delay (not shown). Similar observations were made in cultures amended with lactate, which was readily fermented to acetate, propionate, and H$_2$ before VC dechlorination started.

A VC-dechlorinating culture enriched with acetate as the only available electron donor was also derived from the PCE-to ethene-dechlorinating microcosm. Acetate sustained VC dechlorination for more than 12 consecutive transfers, however, the lag time before dechlorination to ethene occurred was long (3-4 weeks), dechlorination to ethene proceeded very slowly, and no visible growth occurred. Both the acetate-enriched and the lactate-enriched cultures were used to explore VC dechlorination in more detail although the focus was on the high-rate lactate-enriched culture because of its robust VC-dechlorinating activity.

Dechlorination Kinetics and Lag Period

Half-velocity coefficients (K$_S$) and maximum aqueous dechlorination rates (kX) for VC and DCEs determined in pyruvate-fed cultures are shown below:

| Substrate | K$_s$ [μM] | kX [μMday$^{-1}$] |
|---|---|---|
| VC | 5.8 ± 0.4 | 54.4 ± 3.5 |
| cis-DCE | 8.9 ± 0.4 | 23.1 ± 0.8 |
| trans-DCE | 8.5 ± 0.3 | 26.2 ± 0.7 |

Similar VC dechlorination rates were measured with lactate as electron donor, and dechlorination at about half these rates were determined with H$_2$ as the electron donor. In acetate-enriched cultures VC dechlorination was sustained at much lower rates of 2.4±0.5 μmol L$^{-1}$d$^{-1}$. The experimental data for VC and DCE dechlorination were modeled using the Monod equation with the parameters K$_S$ and kX obtained from nonlinear regression analysis. These models suggested that dechlorination followed zero-order kinetics after the lag period at chloroethene concentrations greater than 5 μM.

Similar VC dechlorination rates were observed at temperatures between 22 and 30° C., however, the lag time prior to dechlorination was consistently shorter at 30° C. Dechlorination also occurred at 15° C. but only negligible ethene formation was observed at 4° C. and 35° C. over a 3-month incubation period. The lag time before the onset of VC dechlorination was always at least 10 days, independent of the electron donor added, the initial VC concentration, the reductant used, or the inoculum size (1 to 5% [vol/vol]). No differences in lag periods were observed with commercial cis-DCE or biologically produced cis-DCE. The type and concentrations (0.2-0.5 mM) of chemicals used to reduce the medium (i.e., sulfide, DTT, titanium(III)citrate, L-cysteine) had no effect on the lag periods or the dechlorination rates. The addition of a reductant, however, was essential for dechlorination to occur. To determine if preconditioned medium would support dechlorination with a shorter lag time, actively dechlorinating cultures amended with pyruvate as the electron donor were autoclaved and then seeded with a second inoculum. Again, a similar lag time of at least 10 days was observed. The addition of filter-sterilized medium from an actively dechlorinating culture had no effect on lag time or culture performance.

Dechlorination of Polychlorinated Ethenes.

Although the VC-dechlorinating culture was derived from a PCE-to-ethene-dechlorinating microcosm, the culture failed to dechlorinate PCE and TCE following prolonged enrichment with VC. Interestingly, PCE and TCE were dechlorinated to ethene in cultures that simultaneously received VC, or when added to VC-grown cultures. During dechlorination of PCE and TCE, a transient accumulation of VC and small amounts of 1,1-DCE (<9 μmol), cis-DCE (<5 μmol), and trans-DCE (<1 μmol) was observed. A single passage in medium amended with PCE or TCE, but without DCEs or VC, resulted in a complete loss of dechlorinating activity. In contrast, cultures could be repeatedly transferred in medium amended with cis-DCE, trans-DCE, or 1,1-DCE and still maintained the ability to dechlorinate VC with continued production of ethene. DCEs were dechlorinated to ethene with the intermediate formation of VC.

The tceA gene implicated in TCE dechlorination in *Dehalococcoides ethenogenes* strain 195 was not detected in the VC-dechlorinating Bachman culture supporting the observation that TCE was not used as metabolic electron acceptor. In contrast, the tceA gene was readily detected in *Dehalococcoides ethenogenes* and a TCE-to-VC-reducing river sediment enrichment culture containing a *Dehalococcoides* population.

Identification of the Dechlorinating Population.

In an effort to identify the VC-dechlorinating population(s), 16S rRNA gene primers targeting known chloroethene-dechlorinators were tested on genomic DNA extracted from the enrichment culture. Amplicons of the expected size (620 bp) were obtained in direct PCR with primers targeting the *Dehalococcoides* group. The same primer pair identified five out of 82 clones in 16S rRNA gene clone libraries that also contained 16S rDNA inserts most similar to *Dehalococcoides* 16S rDNA. Restriction fragment length polymorphism (RFLP) and partial sequencing (ca. 800 bp analyzed) of clones containing a *Dehalococcoides* 16S rRNA gene identified two clones with chimeric 16S rDNA inserts. The three remaining clones could not be distinguished by RFLP and sequencing suggesting that the 16S rDNA inserts were derived from a single *Dehalococcoides* population. Nearly complete, double stranded sequence analysis of two cloned 16S rRNA genes yielded identical sequences most similar to *Dehalococcoides* sequences of the Pinellas subgroup (see supra). Shown below is a comparison of the 16S rRNA gene sequence of the VC-dechlorinating *Dehalococcoides* population present in the Bachman culture with those of known *Dehalococcoides* isolates and representative environmental clone sequences:

TABLE 1

Comparison of *Dehalococcoides* 16S rRNA genes.

| 16S rDNA sequence | Group[b] | GenBank accession no. | 1 | 2 | 3 | 4 | 5 | 6 | 7 |
|---|---|---|---|---|---|---|---|---|---|
| | | | | | | Similarity (%) | | | |
| *Dhc. ethenogenes* strain 195 | C | AF004928 | 1 | 99.2 | 98.7 | 98.9 | 98.2 | 98.2 | 98.1 |
| DCEH2[a] | C | AJ249262 | 2 | 10 | 98.8 | 99.0 | 98.2 | 98.2 | 98.1 |

TABLE 1-continued

Comparison of *Dehalococcoides* 16S rRNA genes.

| 16S rDNA sequence | Group[b] | GenBank accession no. | 1 | 2 | 3 | 4 | 5 | 6 | 7 |
|---|---|---|---|---|---|---|---|---|---|
| | | | \multicolumn{7}{c}{Similarity (%)} |
| DHC-vic[a] | V | AF388550 | 3 | 16 | 15 | | 99.8 | 98.8 | 98.8 | 98.7 |
| DHC-dll[a] | V | AF388536 | 4 | 14 | 13 | 2 | | 98.9 | 98.9 | 98.8 |
| *Dhc.* sp. strain CBDB1[c] | P | AF230641 | 5 | 23 | 23 | 15 | 14 | | 100 | 99.9 |
| *Dhc.* sp. strain FL2 | P | AF357918 | 6 | 23 | 23 | 15 | 14 | 0 | | 99.9 |
| *Dhc.* sp. in Bachman culture | P | AY165308 | 7 | 24 | 24 | 16 | 15 | 1 | 1 | |
| | | | \multicolumn{7}{c}{Number of base differences} |

[a]Environmental clone sequence
[b]Group designations according to Hendrickson et al.; C/Cornell, V/Victoria, P/Pinellas sequence subgroups
[c]*Dhc.* sp. strain CBDB1 utilizes chlorinated benzenes, but not PCE or TCE, as electron acceptors.

Evidence for VC-Dependent Growth

Cultures amended with lactate, pyruvate or $H_2$ showed visible growth before dechlorination started, and no measurable increase in optical density (monitored spectrophotometrically at 600 nm) occurred during the period of VC dechlorination. In order to explore whether the *Dehalococcoides* population implicated in VC dechlorination grew with VC as a metabolic electron acceptor, 16S rDNA-based approaches were used. Cultures that were fed with pyruvate and VC contained more PCR-amplifiable *Dehalococcoides* 16S rDNA than cultures that were only fed pyruvate. *Dehalococcoides* 16S rRNA gene targeted RTm PCR confirmed that the increase in *Dehalococcoides* 16S rDNA was dependent on the presence of VC. Actively dechlorinating cultures that had dechlorinated 90 μmol VC contained 51 times $(3.9\pm0.24\times10^5)$ more *Dehalococcoides* 16S rRNA gene copies $ml^{-1}$ than cultures grown under the same conditions without VC $(7.7\pm0.7\times10^3$ copies). The cultures received a 2-ml inoculum containing $7.8\times10^3$ *Dehalococcoides* 16S rRNA gene copies $ml^{-1}$ corroborating that no growth occurred in the absence of VC. Measurements of $H_2$ consumption threshold concentrations provided additional evidence for the metabolic reduction of VC. In the presence of VC, $H_2$ was consumed to concentrations of 0.12 (+/−0.02) ppmv in lactate- and acetate/$H_2$-fed cultures. In contrast, $H_2$ threshold values in cultures grown under the same conditions but without VC were at least two orders of magnitude higher.

Dechlorination in the Presence of Ampicillin

Reductive dechlorination of DCEs and VC to ethene occurred in the presence of ampicillin although dechlorination rates were about one third less than those measured in cultures without the antibiotic. In the presence of ampicillin, reductive dechlorination was strictly dependent on H2 as electron donor, and neither visible growth nor dechlorination occurred with organic electron donors (e.g., lactate, pyruvate, formate).

Analysis of Dechlorination Study

Sediment-free, nonmethanogenic bacterial enrichment cultures catalyzing the final dechlorination step in the reductive dechlorination pathway of chloroethenes leading to complete detoxification (i.e., ethene formation) were obtained from PCE-to-ethene-dechlorinating Bachman microcosms. The 16S rDNA-based analysis implicated a *Dehalococcoides* population in VC reductive dechlorination, a finding that was supported by physiological evidence. First, dechlorination occurred in the presence of ampicillin, and second, dechlorination in ampicillin-amended cultures was strictly dependent on $H_2$ suggesting $H_2$ as the direct electron donor for reductive dechlorination. Both are characteristics of the known *Dehalococcoides* populations. Adrian et al., *Nature*, 2000, 408: 580-583, Maymó-Gatell et al., *Science*, 1997, 276:1568-1571 Although $H_2$ was the direct electron donor for reductive dechlorination, higher dechlorination rates were supported in the pyruvate- or lactate-fed enrichment culture suggesting a supporting role for other populations. This observation may also explain the lower dechlorination rates observed in medium amended with ampicillin, where pyruvate and lactate fermenting populations could not grow. The interactions between the dechlorinator and other populations are unclear but might be nutritional in nature. The nutritional requirements of *Dehalococcoides ethenogenes* are not fully understood, and this organism can only be grown and maintained in medium of undefined composition Maymo-Gatell et al., *Science*, 1997, 276:1568-1571. Hence, further physiological studies leading to an improved understanding of the nutritional requirements of *Dehalococcoides* species are necessary to facilitate isolation and culturability.

The *Dehalococcoides* population present in the Bachman culture exhibited relevant physiological differences in regard to electron acceptor utilization patterns to the known chloroethene dechlorinator *Dehalococcoides ethenogenes* strain 195. *Dehalococcoides ethenogenes* was reported to utilize PCE, TCE, cis-DCE, and 1,1-DCE as metabolic electron acceptors (zero order kinetics), but failed to grow with trans-DCE and VC. trans-DCE and VC, however, were cometabolized by strain 195 in the presence of a growth-supporting chloroethene. Maymó-Gatell et al., *Appl. Environ. Microbiol.*, 1999, 65: 3108-3113; Maymó-Gatell et al., *Environ. Sci., Technol.*, 2001, 35:516-521. An opposite picture was seen with the *Dehalococcoides* population present in the Bachman enrichment. All DCEs and VC were readily dechlorinated to ethene but PCE and TCE were only reduced in the presence of lower chlorinated ethenes, presumably in a cometabolic reaction. In support of this observation, tceA, the gene encoding the TCE reductive dechlorinase implicated in dechlorination of TCE and DCEs in *Dehalococcoides ethenogenes*, was not detected in the Bachman culture. Magnuson, *Appl. Environ. Microbiol.*, 2000, 66:5141-5147. These findings demonstrate that *Dehalococcoides* populations with different substrate specificities towards chlorinated ethenes exist, and confirm observations that the complete reductive dechlorination process is most efficiently carried out by more than one population. See e.g., Duhamel et al., *Water Res.*, 2002, 36:4193-4202.

A few studies already provided circumstantial evidence that VC serves as a metabolic electron acceptor, and that *Dehalococcoides* populations are involved in ethene formation. See e.g., Duhamel et al., *Water Res.*, 2002, 36:4193-

4202. The results of this study present conclusive evidence that the *Dehalococcoides* population identified in the Bachman culture grew with VC as a metabolic electron acceptor. Growth of the *Dehalococcoides* population with VC was confirmed by (i) the VC-dependent increase in the number of *Dehalococcoides* 16S rRNA genes, (ii) the loss of dechlorinating activity when transferred in the same medium without VC, (iii) the disappearance of VC following zero-order kinetics, and (iv) $H_2$ consumption threshold measurements. After more than 40 transfers with lactate as the source of reducing equivalents, the culture lost the ability to reduce VC with acetate as the only electron donor, presumably because the population(s) implicated in syntrophic acetate oxidation was lost in the enrichment process. He et al., *Environ. Sci., Technol.,* 2002, 36:3945-3952. Hence, no intrinsic $H_2$ formation from acetate occurred, and the measured values represent true $H_2$ consumption threshold concentrations rather than compensation concentrations. Löffler et al., *Appl. Environ. Microbiol,* 1999, 65:4049-4056. The $H_2$ consumption threshold concentration determined for the VC-dechlorinating Bachman culture was similar to $H_2$ threshold concentrations determined for other hydrogenotrophic chloridogenic populations Löffler, et al., *Appl. Environ. Microbiol.,* 1999, 65:4049-4056; Sanford et al., *Appl. Environ. Microbiol,* 2002, 68: 893-900.

In a recent study, Hendrickson et al. recovered at least one *Dehalococcoides* 16S rDNA sequence from all chloroethene-contaminated sites where complete reductive dechlorination occurred. Hendrickson et al., *Appl. Environ. Microbiol.,* 2002, 68: 485-495 Based on signature sequences identified in variable regions II and VI of the 16S rRNA gene, these authors distinguished *Dehalococcoides* spp. into a Cornell, Victoria, and Pinellas sequence subgroup. The 16S rRNA gene sequence of the VC-dechlorinating population in the Bachman enrichment is nearly identical with the Pinellas subgroup sequences, except for a transition (G→A) at *E. coli* position 148, as shown above.

Since Hendrickson et al. performed no physiological characterizations, this study did not distinguish metabolic VC dechlorinators from those *Dehalococcoides* populations that cannot grow with VC. Additional *Dehalococcoides* populations that grow with VC as electron acceptor must be identified to determine if this transition is characteristic for VC-respiring *Dehalococcoides* strains, and is a useful diagnostic tool. Table 1 demonstrates that *Dehalococcoides* populations share very similar 16S rRNA genes, implying that focusing exclusively on 16S rRNA gene analysis may be insufficient to distinguish *Dehalococcoides* populations with different dechlorination activities, and to predict the potential for complete microbial detoxification of chloroethenes (i.e., ethene formation) at contaminated sites. For instance, *Dehalococcoides* sp. strain CBDB1 is a member of the Pinellas group and uses chlorobenzenes as electron acceptors but failed to grow with chloroethenes. Adrian et al., *Nature,* 2000, 408: 580-583.

The physiological characteristics of *Dehalococcoides ethenogenes*-type populations are reason for concern because VC is not used as metabolic electron acceptor, and cometabolic VC reduction requires the presence of higher chlorinated ethenes. Indeed, the reductive dechlorination of polychlorinated ethenes along with the accumulation of VC has been observed at numerous sites. Hendrickson et al., *Appl. Environ. Microbial.,* 2002, 68:485-495; Wilson et al., Document EPA/600/R-95/076, available on the Worldwide Web at http//Itoxics.usgs.gov/bib/bid-pica-year.Html#1995. Hence, the type of *Dehalococcoides* population present in the Bachman enrichment culture seems desirable for bioremediation at many chloroethene-contaminated sites because VC serves as growth-supporting electron acceptor, and dechlorination is sustained in VC plumes not containing PCE, TCE, or DCEs. To overcome the limitations of the 16S rDNA approach, future research must focus on the identification of functional genes that are specific for the process of interest, and distinguish *Dehalococcoides* populations with different dechlorinating activities. This data is important for providing information on whether biostimulation or bioaugmentation is the most promising approach at any particular chloroethene-contaminated site amenable to bioremediation technologies.

Patents, patent applications, publications, product descriptions, and protocols are cited throughout this application, the disclosures of which are incorporated herein by reference in their entireties for all purposes.

What is claimed is:

1. A method of quantifying the amount of a plurality of different *Dehalococcoides* species present in a sample comprising, contacting said sample with:
   (i) a probe comprising the sequence 5'TCCTCAGTTCG-GATTGCAGGCTGAA3' (SEQ ID NO: 1);
   (ii) a first primer comprising the sequence 5'CTG-GAGCTAATCCCCAAAGCT3' (SEQ ID NO: 2); and
   (iii) a second primer comprising the sequence 5'CAACT-TCATGCAGGCGGG3' (SEQ ID NO: 3); and
   performing real time PCR on said sample to quantify the amount of said plurality of different *Dehalococcoides* species.

2. The method of claim 1, wherein the probe comprises a reporter dye.

3. The method of claim 2, wherein the reporter dye is 6-carboxyfluorescein.

4. The method of claim 1, wherein the probe comprises a quencher dye.

5. The method of claim 4, wherein the quencher dye is 6-carboxytetramethylrhodamine.

6. The method of claim 1, wherein the real time PCR reaction comprises a 2 minute incubation at 50° C., a 10 minute incubation at 95° C, and 40 cycles of 15 second incubations at 95° C. followed by 1 minute incubations at 60° C.

7. The method of claim 1, wherein the sample comprises DNA extracted from a soil sample.

8. The method of claim 1, wherein the sample comprises DNA extracted from a water sample.

9. The method of claim 1, wherein the probe consists of the sequence 5'TCCTCAGTTCGGATTGCAGGCTGAA3' (SEQ ID NO: 1).

10. The method of claim 1, wherein the first primer consists of the sequence 5'CTGGAGCTAATCCCCAAAGCT3' (SEQ ID NO: 2).

11. The method of claim 1, wherein the second primer consists of the sequence 5'CAACTTCATGCAGGCGGG3' (SEQ ID NO: 3).

12. The method of claim 1, wherein the first primer consists of the sequence 5'CTGGAGCTAATCCCCAAAGCT3' (SEQ ID NO: 2) and the second primer consists of the sequence 5'CAACTTCATGCAGGCGGG3' (SEQ ID NO: 3).

13. A method of quantifying the amount of a plurality of different *Dehalococcoides* e species present in a sample comprising, contacting said sample with:
   (i) a probe that consists of the sequence 5'TCCTCAGT-TCGGATTGCAGGCTGAA3' (SEQ ID NO: 1);
   (ii) a first primer that consists of the sequence 5'CTG-GAGCTAATCCCCAAAGCT3' (SEQ ID NO: 2); and
   (iii) a second primer that consists of the sequence 5'CAACTTCATGCAGGCGGG3' (SEQ ID NO: 3); and
   performing real time PCR on said sample to quantify the amount of said plurality of different *Dehalococcoides* species.

14. The method of claim 13, wherein the probe comprises a reporter dye.

15. The method of claim 14, wherein the reporter dye is 6-carboxyfluorescein.

16. The method of claim 13, wherein the probe comprises a quencher dye.

17. The method of claim 16, wherein the quencher dye is 6-carboxytetramethylrhodamine.

18. The method of claim 13, wherein the real time PCR reaction comprises a 2 minute incubation at 50° C., a 10 minute incubation at 95° C., and 40 cycles of 15 second incubations at 95° C. followed by 1 minute incubations at 60° C.

19. The method of claim 13, wherein the sample comprises DNA extracted from a soil sample.

20. The method of claim 13, wherein the sample comprises DNA extracted from a water sample.

* * * * *